United States Patent [19]

Hirai et al.

[11] Patent Number: 4,940,660

[45] Date of Patent: Jul. 10, 1990

[54] COLOR DEVELOPING METHOD IN CLINICAL EXAMINATIONS

[75] Inventors: Hidematsu Hirai, Mitaka; Toshiro Hanada, Kawagoe; Kazuhiko Yamanishi, Tokyo; Hideko Nohara, Asaka, all of Japan

[73] Assignee: Wako Pure Chemical Industries, Osaka, Japan

[21] Appl. No.: 914,834

[22] Filed: Oct. 2, 1986

[30] Foreign Application Priority Data

Nov. 25, 1985 [JP]   Japan ................................ 60-264142
Jun. 17, 1986 [JP]   Japan ................................ 61-141057

[51] Int. Cl.$^5$ .................. G01N 33/53; C12Q 1/28; C12Q 1/26
[52] U.S. Cl. ........................................ 435/7; 435/28; 435/25
[58] Field of Search .................... 435/4, 7, 28, 25, 26

[56] References Cited

U.S. PATENT DOCUMENTS

| | | | |
|---|---|---|---|
| 4,350,762 | 9/1982 | De Luca et al. | 435/10 |
| 4,592,996 | 5/1986 | Yamanishi et al. | 435/11 |

FOREIGN PATENT DOCUMENTS

| | | |
|---|---|---|
| 2033082A | 5/1980 | European Pat. Off. . |
| 0100217 | 8/1984 | European Pat. Off. . |
| 0124909A2 | 11/1984 | European Pat. Off. . |
| 86113651.3 | 2/1987 | European Pat. Off. . |

OTHER PUBLICATIONS

Sevier, E. D., et al., Clin. Chem., vol. 27, No. 11, pp. 1797–1806 (1981).
Michal, G., Möllering, H., Siedel, J., "Chemical Design of Indicator Reactions for the Visible Range", In Methods of Enzymatic Analysis, Third Edition, (Bergmeyer, ed). vol. I (Dec. 1985) pp. 197–221.

*Primary Examiner*—Robert J. Warden
*Assistant Examiner*—Toni R. Scheiner
*Attorney, Agent, or Firm*—Armstrong, Nikaido, Marmelstein, Kubovcik & Murray

[57] ABSTRACT

A process for the determination of peroxidase activity or hydrogen peroxide in a clinical sample colorometrically by adding to the sample a reduced form coenzyme, a reagent selected from amines, phenols, and naphthols, a compound which is colored in the reduced form, and peroxidase or an aqueous solution of hydrogen peroxide. The process is essentially unaffected by the presence of ascorbic acid, bilirubin or other reducing substances of body fluids.

12 Claims, 8 Drawing Sheets

COLOR DEVELOPING METHOD IN CLINICAL EXAMINATIONS

BACKGROUND OF THE INVENTION

This invention relates to a process for measuring the degree of coloring of a color developing reagent to be reduced such as tetrazolium compounds in determination of the amount of hydrogen peroxide generated or peroxidase activity in clinical examinations.

Detection and determination of hydrogen peroxide ($H_2O_2$) are very important not only in chemical experiments and industrial applications but also in widely used clinical examinations wherein determination of living body components is carried out by determining $H_2O_2$ generated by enzymatic reactions. For example, the amounts of cholesterol, triglyceride, glucose, uric acid, phospholipids, bile acid, choline esterase, monoamine oxidase, guanase, etc., are measured by determining $H_2O_2$ finally produced in individual detective (or determination) systems. Such methods are applied to diagnoses of diseases.

The most widely used method for determining $H_2O_2$ is to use peroxidase and an oxidizable color reagent as a color developing component to develop a color, which is measured colorimetrically for indirectly determining the amount of desired components. Typical examples of the oxidizable color reagents used in this method are a combination of 4-aminoantipyrine and a phenolic compound or an N,N-disubstituted aniline compound; a combination of 3-methyl-2-benzothiazolinone hydrazone (MBTH) and an aniline compound; 2,2'-azino-bis-(3-ethylbenzothiazoline-6-sulfonic acid) (ABTS); triphenylmethane series leuco dyes; benzidine derivatives; diphenylamine derivatives; triarylimidazole derivatives; o-phenylenediamine; etc.

But when these oxidizable color reagents were used in determination of trace components in living body samples such as tisses, body fluid, etc., there took place negative errors in measured values due to an influence of a reduction reaction caused by a reductive substance such as ascorbic acid, bililubin, etc. present in a sample of living bodies. In order to remove such interfering substances, there have been proposed various methods, for example, the use of ascorbate oxidase, an iodate, copper ion-peroxidase-amino compound, etc. to remove ascorbic acid, and the use of potassium ferrocyanide, bilirubin oxidase, etc. to remove bilirubin. But such proposals had a merit and a demerit.

Further, the above-mentioned determination method of $H_2O_2$ is often applied to measuring of individual lipids contained in lipoprotein fractions so as to stain individual lipids by color development by means of an enzymatic method using an oxidizable color reagent. For example, in the case of cholesterol, staining is conducted by using cholesterol oxidase to produce $H_2O_2$, which is reacted with 4- aminoantipyrine and a phenolic compound in the presence of peroxidase (hereinafter referred to as "POD"). But such a method as using an oxidizable color reagent for staining of lipoprotein fractions has a serious problem in staining properties, since a part of produced dye is washed away in a washing step in aftertreatment.

On the other hand, peroxidase (POD) is used as an oxidizing catalyst in enzyme analysis methods using oxidases for producing hydrogen peroxide ($H_2O_2$) in clinical examinations. Recently, POD has widely been used as a labeled enzyme in an immunoenzymatic staining method and enzyme immunoassay. Further, a method for specifically detecting trace amounts of proteins in a living body by using an enzyme (e.g. POD) labeled antibody and by combining electrophoresis with blotting operations has been noted as an epoch-making protein analysis method.

These immunological methods are excellent in specificity, so that application of these methods may be broadened more and more in the future.

The immunoenzymatic staining methods using POD include typically a peroxidase-antiperoxidase complex (PAP) method which is generally used in a histological immunoenzymatic staining method wherein an immune reaction is applied to tissue slices, an avidin-biotin-peroxidase labeling (ABC) method, etc. The final staining in these methods is based on a color reaction in a $H_2O_2$-oxidizable color reagent system applying POD activity.

The enzyme immunoassay using POD is a method comprising measuring POD activity of a POD labeled antibody bonded to a substance to be measured using a $H_2O_2$-oxidizable color reagent and obtaining the concentration of the substance to be measured from the activity value measured.

These methods mainly use oxidizable color reagents such as o-phenylenediamine, 3,3'-diaminobenzidine, 4-chloro-1-naphthol, 3-amino-9-ethylcarbazole, etc. But these methods using the oxidizable color reagents sometimes cause negative errors in measured values by the influence of reducing substances such as ascorbic acid, bilirubin, etc. present in samples, when applied to determination of trace amounts of components present in living bodies. In order to remove these interfering substances, various proposals have been made; for example, ascorbic acid is removed by ascorbate oxidase and an iodate, and bilirubin is removed by potassium ferrocyanide and bilirubin oxidase. But such proposals had a merit and a demerit.

In various detecting and determining methods for various trace amounts of proteins by using electrophoresis and blotting operations in combination, a $H_2O_2$-oxidizable color reagent (such as 3,3'-diaminobenzidine, 4-chloro-1-naphthol, etc.) system is used for measuring activity of POD which is a labeled enzyme. But such methods are not satisfactory in sensitivity and color tone.

Further, many of these oxidizable color reagents are unstable and have a defect in that stained samples to be measured are faded during storage particularly in the histological immunoenzymatic staining method.

On the other hand, the use of a color producing reagent to be reduced is disclosed in European Patent Appln. Laid-Open No. 0100217 in the determination of super oxide anion. But such a method could not be applied to the determination of the amount of $H_2O_2$ or peroxidase activity.

SUMMARY OF THE INVENTION

It is an object of this invention to provide a process for measuring the degree of coloring of a color developing reagent to be reduced such as a tetrazolium compound in a determination of the amount of $H_2O_2$ generated or peroxidase activity with high precision in clinical analyses by removing the influences of reductive substances such as ascorbic acid, bilirubin, etc., present in samples.

This invention provides a process for measuring the degree of coloring of a color producing reagent to be reduced used in determination of the amount of hydrogen peroxide or peroxidase activity in clinical analyses, which comprises adding to a sample a reagent composition comprising (a) a reduced form coenzyme, (b) an amine or a phenol or a naphthol, (c) a color producing reagent to be reduced and (d) peroxidase or an aqueous solution of hydrogen peroxide, and measuring the degree of coloring.

DESCRIPTION OF THE PREFERRED EMBODIMENTS

Figure 1:
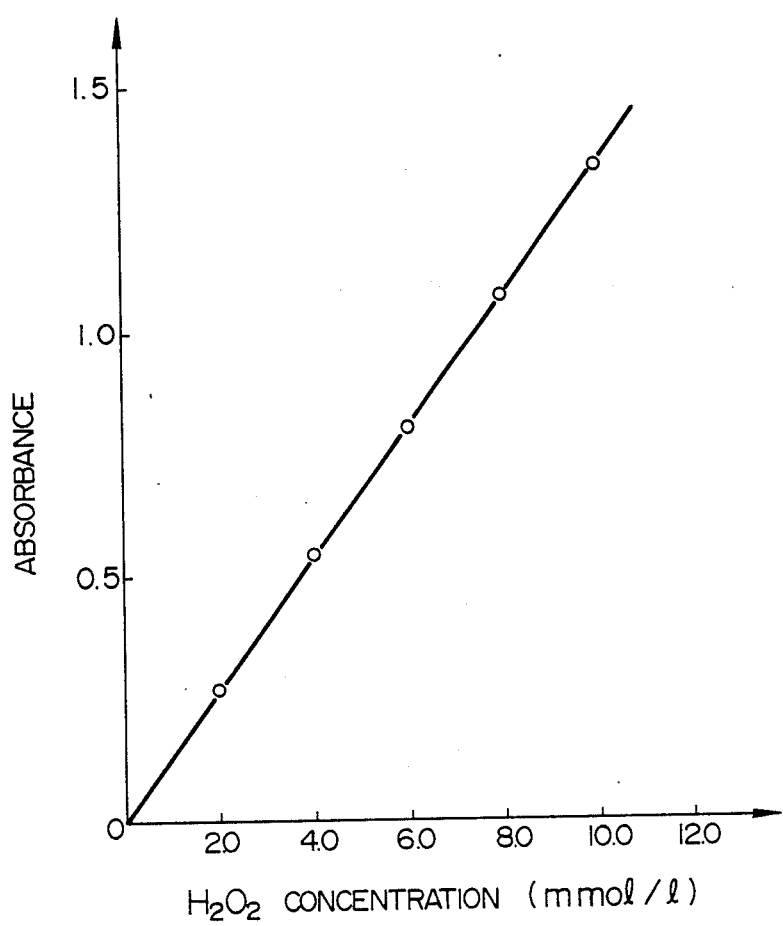
FIG. 1 shows a calibration curve obtained in Example 1.

When the amount of $H_2O_2$ in a sample or a reaction system is determined according to this invention, a reagent solution comprising (a) a reduced form coenzyme, (b) an amine or a phenol or a naphthol, (c) a color producing reagent to be reduced and (d) peroxidase is added to a sample containing $H_2O_2$ or a system to produce $H_2O_2$, then incubated at 15°–40° C., preferably at 25°–40° C., for a predetermined time, followed by measurement of the degree of coloring.

On the other hand, when POD activity is measured according to this invention, a reagent solution comprising (a) a reduced form coenzyme, (b) an amine or a phenol or a naphthol, (c) a color producing reagent to be reduced, and if necessary a surface active agent, is added to a sample, followed by addition of an aqueous $H_2O_2$ solution to the sample. Then an incubation is carried out at a predetermined temperature for a predetermined time, and a reaction stopper (e.g. an acid such as hydrochloric acid, sulfuric acid, etc., sodium dodecylsulfate, etc.) is added to the reaction system to stop the enzymatic reaction, followed by measurement of the degree of coloring.

Further, in the case of an immunoperoxidase staining method, a staining operation is conducted in the same manner as mentioned above, washing is conducted, and then a color tone of the stained portion is observed with or without a microscope or densitometer.

The color development in the process of this invention is not reduction color development of the color developing reagent to be reduced by the simple action of the reduced form coenzyme. This is clear from the facts that no diaphorase or no electron carrier such as phenazine methosulfate (PMS), 1-methoxyphenazine methosulfate (1-methoxy PMS), is present in the reaction system, and no color is developed when reacted by using a color developing reagent solution containing no amine, nor phenol, nor naphthol, (i.e. comprising a reduced form coenzyme, a color producing reagent to be reduced, peroxidase and an aqueous $H_2O_2$ solution). Further, since the reaction is not inhibited by the addition of superoxide dismutase, it is clear that the color development is not due to superoxide ions.

The fact that the color developing reagent to be reduced is quantitatively reduced to develop a color depending on the amount of $H_2O_2$ or POD activity is quite a surprising thing.

As the reduced form coenzyme, there can be used nicotinamide adenine dinucleotide reduced form (NADH), nicotinamide adenine dinucleotidephosphate (NADPH), etc. The reduced form coenzyme is preferably used in an amount of 0.01 to 20 mmol/liter.

As the amine, there can be used conventional organic amines, irrespective of primary, secondary and tertiary amines. Generally speaking, aromatic amines are more effective than aliphatic amines with smaller amounts. Examples of the amines are aniline, N-methylaniline, N-ethylaniline, N,N-dimethylaniline, N,N-diethylaniline, N,N-diethyl-m-toluidine, N-ethyl-N-($\beta$-hydroxyethyl)-m-toluidine, 3,5-dimethoxy-N-ethyl-N-(2-hydroxy-3-sodium sulfopropyl)aniline, sodium N-ethyl-N-(2-hydroxy-3-sulfopropyl)-m-toluidine (TOOS), etc.

As the phenols, there can be used phenol; alkyl-substituted phenols wherein the alkyl is methyl, ethyl, propyl, etc.; alkoxy-substituted phenols wherein the alkoxy is methoxy, ethoxy, propoxy, etc.; halogen-substituted phenols wherein the halogen is chlorine, bromine, fluorine, and iodine; phenolic acids e.g. salicylic acid, p-hydroxybenzoic acid; phenolsulfonic acid, etc.

As the naphthols, there can be used $\alpha$-naphthol, $\beta$-naphthol, naphthol derivatives such as 1-naphthol-2-carboxylic acid, 2-naphthol-3-carboxylic acid, 2-naphthol-6,8-disulfonic acid dipotassium salt, 1-naphthol-3,6-disulfonic acid disodium salt, 2-naphthol-3,6-disulfonic acid disodium salt, 1-naphthol-2-sulfonic acid sodium salt, 1-naphthol-4-sulfonic acid sodium salt, 1-naphthol-5-sulfonic acid sodium salt, 1-naphthol-8-sulfonic acid sodium salt, 2-naphthol-6-sulfonic acid sodium salt, etc.

The amines, phenols and naphthols can be used alone or as a mixture thereof. Further, there can be used compounds having both phenol moiety and amine moiety in their molecules such as 1-N,N-dimethylamino-4-naphthol, 4-N,N-diethylaminosalicylic acid, etc. But when a substrate is an amine, L-amino acid, or the like, and an oxidase is amine oxidase, L-amino acid oxidase, or the like, it is natural to use a phenol, not an amine.

The amines, phenols and naphthols are usually used in an amount of 0.08 to 160 moles, preferably 0.1 to 30 moles, per mole of the reduced form coenzyme.

As the color developing reagent to be reduced, there can be used tetrazolium salts such as 3-(p-iodophenyl)-2-(p-nitrophenyl)-5-phenyl-2H tetrazolium chloride (INT), 3-(4,5-dimethyl-2-thiazolyl)-2,5-diphenyl-2H tetrazolium bromide (MTT), 3,3'-(4,4'-biphenylene)-bis(2,5-diphenyl-2H tetrazolium chloride) (Neo-TB), 3,3'-(3,3'-dimethoxy-4,4'-biphenylene)-bis[2-(p-nitrophenyl)-5-phenyl-2 H tetrazolium chloride] (nitro-TB), 3,3'-(3,3'-dimethoxy-4,4'-biphenylene)-bis(2,5-diphenyl-2H tetrazolium chloride) (TB), 3,3'-(3,3'-dimethoxy-4,4'-biphenylene)-bis[2,5-bis(p-nitrophenyl)-2H tetrazolium chloride] (TNTB), etc. It is also possible to use water-soluble tetrazolium salts such as 2-(2-benzothiazolyl)-3-(o-carboxyphenyl)-5-[p-{hydroxy poly- (oxy-1,2-ethanediyl)} phenyl]-2H tetrazolium chloride, etc.

In the determination of the amount of $H_2O_2$, peroxidase is used as the component (d) in the reagent composition. As the peroxidase, there can be used those derived from plants, animals and microorganisms. Among them, the use of horseradish peroxidase is preferred. The peroxidase is used in an amount of 100 to 10,000 U/liter in the liquid amount at the time of color development.

The pH for the determination of $H_2O_2$ amount is preferably 4 to 9 considering the stability of enzymes used.

Substrates to be measured by the determination of $H_2O_2$ amount are glucose, galactose, cholesterol, glycerol, glycerophosphate, choline, acyl CoA, pyruvic acid, uric acid, xanthine, lactic acid, sarcosine, oxalic acid, etc. In the determination of the substrates, an oxidase acting on a substrate to be measured is used. Examples of oxidases in the order of the substrates mentioned above are glucose oxidase, galactose oxidase, cholesterol oxidase, glycerol oxidase, glycerophosphate oxidase, choline oxidase, acyl CoA oxidase, pyruvate oxidase, uricase, xanthine oxidase, lactate oxidase, sarcosine oxidase, oxalate oxidase, etc.

In order to fractionate lipoprotein, there is used agarose gel, agar gel, cellulose acetate, polyacrylamide gel, etc., as a supporter lipoprotein is fractionated by electrophoresis, then individual lipids contained in lipoprotein fractions are stained according to the process of this invention, followed by colorimetrical determination.

One example of the staining determination method is as follows. A reagent solution obtained by dissolving the reagent composition of this invention (peroxidase is used as the component (d)) is impregnated in sheets of filter paper. Front side and rear side of a separating strip is sandwiched by the thus obtained filter paper or the reagent solution is applied on the separating strip followed by a reaction at 37° C. for 30 minutes in an incubator. Then, the reagent solution on the strip is sufficiently shaken off, and the strip is dipped in an admixed solution of ethanol:acetic acid:water (14:1:5 by volume) for about 30 minutes with stirring, followed by washing with water for about 30 minutes. Then, the gel is subjected to densitometric scanning with densitometer for the determination after drying or as it is.

In order to measure the POD activity, $H_2O_2$ is used as the component (d) of the reagent composition. Practically, an aqueous $H_2O_2$ solution prepared separately is used. It is preferable to use $H_2O_2$ in an amount of 1.0 to 7.5 moles per mole of the reduced form coenzyme.

The process for measuring POD activity of this invention can effectively be used in the immunoperoxidase staining method such as PAP method, ABC method, etc., and in the enzyme immunoassay (EIA method).

In the immunoperoxidase staining method, the reagent composition comprising (a) a reduced form coenzyme, (b) an amine, or a phenol or a naphthol, (c) a color producing reagent to be reduced, and (d) $H_2O_2$ is used in place of $H_2O_2$ and an oxidizable color producing reagent conventionally used. Other conditions and procedures are the same as those used in a conventional method using the oxidizable color producing reagent. In the EIA method, the reagent composition comprising (a) a reduced form coenzyme, (b) an amine, or a phenol, or a naphthol, (c) a color producing reagent to be reduced, and (d) $H_2O_2$ is also used in place of $H_2O_2$ and an oxidizable color developing reagent conventionally used. Other conditions and procedures are also the same as those used in a conventional method using the oxidizable color producing reagent.

According to this invention, an oxidizable color producing reagent used in a conventional method is replaced by a color producing reagent to be reduced such as a tetrazolium compound, which is color developed in the presence of a reduced form coenzyme, an amine or a phenol or a naphthol, peroxidase and $H_2O_2$ A formazan compound formed by the reduction of the tetrazolium salt shows a color of yellow to blue depending on its structure. Many of the formazan compounds formed are hardly soluble in water, so that they are very advantageous in the immunoenzymatic staining method. Further, in the case of colorimetric determination in an aqueous solution such as the enzyme immunoassay, it is possible to make the formazan compound water-soluble by the addition of gelatine or a surface active agent. Therefore, there is no inconvenience in practical use. Or, in such a case, it is possible to use a tetrazolium salt which can produce a water-soluble formazan compound.

According to the POD activity measuring process of this invention, it is possible to use a wide range of pH from acidic to alkaline. Considering the stability of enzymes, pH of 4 to 9 is preferable.

Objects measurable by the EIA method applying the process of this invention are physiologically active substances measurable according to the conventional EIA method, for example, α-fetoprotein, carcinoembryonic antigen (CEA), proteins such as IgG, insulin, growth hormone, human chorionic gonadotropin (hCG), thyroxine, hormones such as thyroid stimulating hormone, antibodies such as HBs antibody, antigens such as HBs antigen, digoxin, morphine, etc.

Objects measurable by the immunoperoxidase staining method applying the process of this invention are antigens which are able to be stained by a conventional immunoperoxidase staining method, for example, various immunoglobulins, lymphocyte cell membrane antigen, hormone-forming cells, intracellular enzymes, antigens derived from foetus, virus antigens, etc.

Further, since it is possible to measure peroxidase-like substances according to the process of this invention, it is possible to determine the amount of hemoglobin.

This invention is illustrated by way of the following Examples.

EXAMPLE 1

(Determination of $H_2O_2$)

A color developing reagent solution was prepared by dissolving 0.67 mmol/l. of NADH, 2000 U/l. of peroxidase, 0.02% w/v of phenol, 0.05% w/v of Triton X-100 polyoxyethylene (10) octylphenyl ether (trademark of Rohm and Haas Co.), and 200 mg/l. of nitro-TB in 0.05 M tris(hydroxymethyl)aminomethane-HCl buffer (pH 7.0).

Aqueous solution containing 2.0, 4.0, 6.0, 8.0 and 10.0 mmol/l of $H_2O_2$, respectively, were prepared as samples.

To a 20 μl of sample, 3.0 ml of the color developing reagent solution was added and incubated at 37° C for 10 minutes, followed by measurement of absorbances at 560 nm using reagent blank as control.

FIG. 1 shows a relationship between the $H_2O_2$ concentration and the absorbance. As is clear from FIG. 1, a calibration curve obtained by lining plots of absorbances corresponding to individual $H_2O_2$ concentrations (mmol/l) is a linear line passing through the origin. This means that the calibration curve shows good quantitativeness.

EXAMPLE 2

(Determination of Free Cholesterol in Serum)

A color developing reagent solution was prepared by dissolving 0.67 mmol/l of NADH, 150 U/l of cholesterol oxidase, 2000 U/l of peroxidase, 0.02% w/v of phenol, 0.05% w/v of Triton X-100 and 200 mg/l of nitro-TB in 0.05 M tris(hydroxymethyl)aminomethane-HCl buffer (pH 7.0).

To serum (containing no ascorbic acid) in an amount of 20 μl, 3.0 ml/l of the color developing reagent solution was added and incubated at 37° C. for 10 minutes, followed by measurement of absorbance at 560 nm using reagent blank as control.

Figure 2:
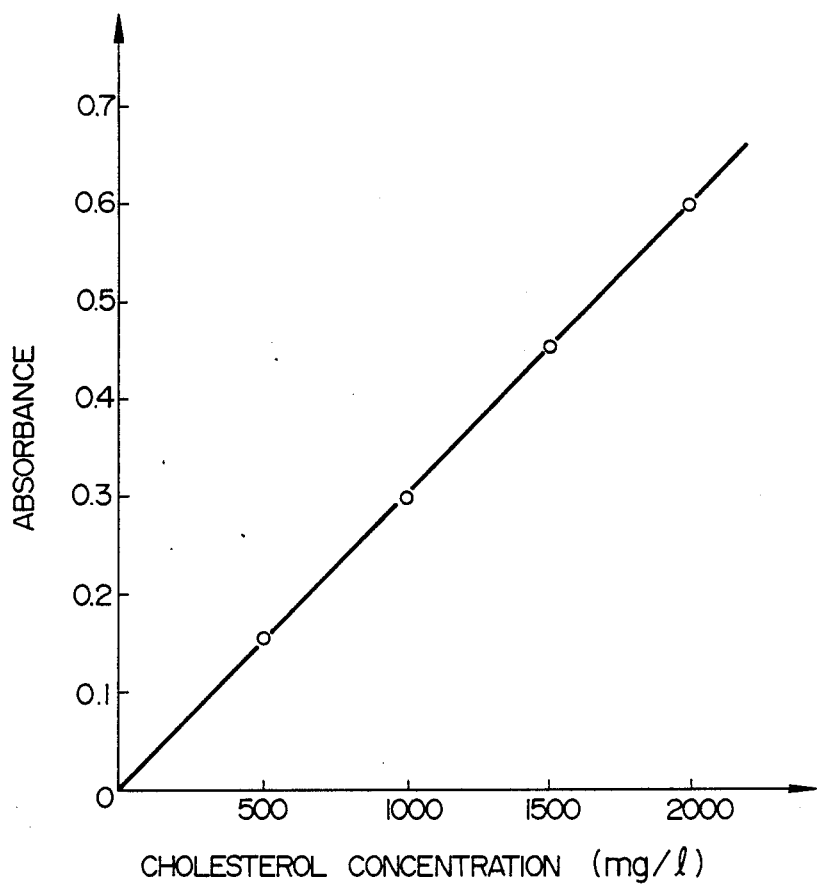
FIG. 2 shows a calibration curve obtained in Example 2.

On the other hand, cholesterol standard solutions were prepared by making the concentration of cholesterol in isopropanol 500, 1000, 1500 and 2000 mg/l respectively. A 20-μl standard solution was treated in the same manner as mentioned above to obtain a calibration curve as shown in FIG. 2 from the absorbances obtained. Free cholesterol concentration in serum was obtained from FIG. 2.

Measured results are shown in Table 1.

REFERENCE EXAMPLE 1

(Determination of Free Cholesterol in Serum)

A color developing reagent solution was prepared by dissolving 0.1% w/v of phenol, 0.01% w/v of 4-aminoantipyrine, 100 U/l of cholesterol oxidase, 3000 U/l of peroxidase, and 0.15% w/v of Triton X-100 in 0.1 M of phosphate buffer (pH 7.0).

To each 50 μl of the same serum as used in Example 2, 3 ml of the color developing reagent solution was added and incubated at 37° C. for 15 minutes, followed by measurement of absorbance at 505 nm using reagent blank as control (Ex). Using a cholesterol standard solution (cholesterol 1,000 mg/l ), absorbance (Es) was obtained in the same manner as described in the procedure of serum to calculate the free cholesterol concentration in serum by the following equation:

$$\text{Cholesterol concentration (mg/l)} = \frac{Ex}{Es} \times 1{,}000$$

Measured results are also shown in Table 1.

As shown in Table 1, the values obtained in Example 2 are in good agreement with those of Reference Example 1 and no significant difference is admitted.

TABLE 1

| Serum No. | Example 2 [X] | Reference Example 1 [Y] |
|---|---|---|
| 1 | 470 (mg/l) | 490 (mg/l) |
| 2 | 370 | 370 |
| 3 | 480 | 510 |
| 4 | 340 | 330 |
| 5 | 710 | 730 |
| 6 | 690 | 690 |
| 7 | 390 | 400 |
| 8 | 400 | 410 |
| 9 | 590 | 570 |
| 10 | 360 | 360 |
| Average | 480 | 486 |

TABLE 1-continued

| Serum No. | Example 2 [X] | Reference Example 1 [Y] |
|---|---|---|
| SD | 137 | 139 |

Y = 1.01X + 0.6 (γ = 0.994)

EXAMPLE 3

[Lipoprotein Fractional Staining Method (total cholesterol staining)]

A staining reagent solution was prepared by dissolving 250 U/l of cholesterol esterhydrolase, 800 U/l of cholesterol oxidase, 6,000 U/l of peroxidase, 0.7 mmol/l of NADH, 0.05% w/v of nitro-TB, 0.03% w/v of TOOS and 0.02% w/v of Triton X-100 in 0.05 M phosphate buffer (ph 7.0).

[Electrophoresis]

Using agarose gel as a supporter (5.5×7 cm), serum samples ①, ②, ③ in amounts of 4 μl, respectively, were applied to the gel. A veronal-sodium veronal buffer solution (pH 8.6, ionic strength 0.05) was used as a buffer solution for migration, and electrophoresis was conducted at 30 mA/plate for 30 minutes.

[Staining]

On the agarose gel plate after electrophoresis, the staining reagent solution was applied, incubated at 37° C. for 30 minutes, subjected to removing of the staining reagent solution, and dipped in a 10% acetic acid. After washing with water, the agarose gel was taken out and subjected to air-drying on a glass plate.

Figure 3:
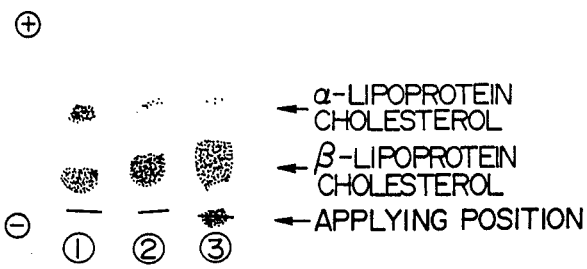
FIG. 3 shows cholesterol stained bands in lipoprotein fractions obtained in Example 3.

The cholesterol was stained in violet. FIG. 3 shows typical cholesterol stained patterns in lipoprotein fractions, wherein ⊕ means an anode side and ⊖ means a cathode side at the time of electrophoresis, and numerals ① to ③ means sample numbers.

Figure 4:
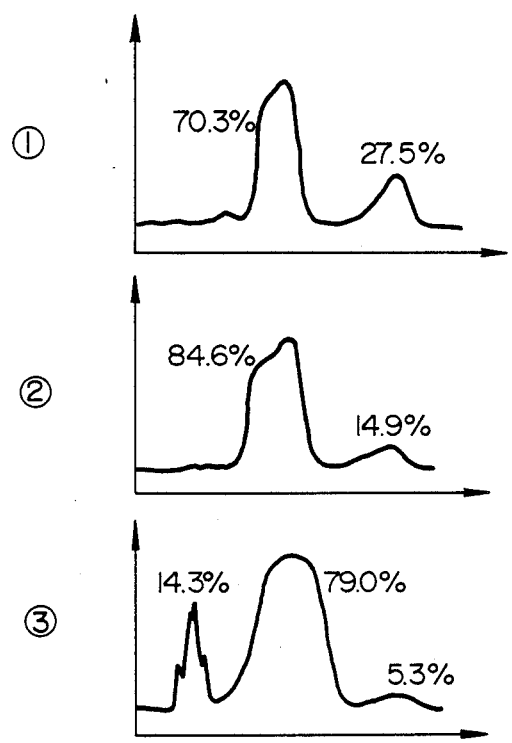
FIG. 4 is densitogram of stained bands obtained in Example 3 measured by using a densitometer.

The lipoprotein fractional stained bands obtained above were measured with a densitometer to obtain a cholesterol ratio of α,β-lipoproteins and showed in FIG. 4. In FIG. 4, numerals ① to ③ attached to the densitograms correspond to sample Nos. ① to ③ obtained in FIG. 3. As the densitometer, there was used Densitometric 8 HD-220 (filter 570 nm; mfd. by Hikari Densoku K.K.).

EXAMPLE 4

(Determination of Glucose in Serum)

A color developing reagent solution was prepared by dissolving 1.0 mmol/l of NAND, 30,000 U/l of glucose oxidase, 3,000 U/l of peroxidase, 0.05% w/v of TOOS, and 200 mg/l of INT in 0.1 M phosphate buffer (pH 7.0).

To 10 μl of serum (containing no ascorbic acid), 3.0 ml of the color producing reagent solution was added and incubated at 37° C. for 20 minutes, followed by measurement of absorbance at 500 nm using reagent blank as control.

Figure 5:
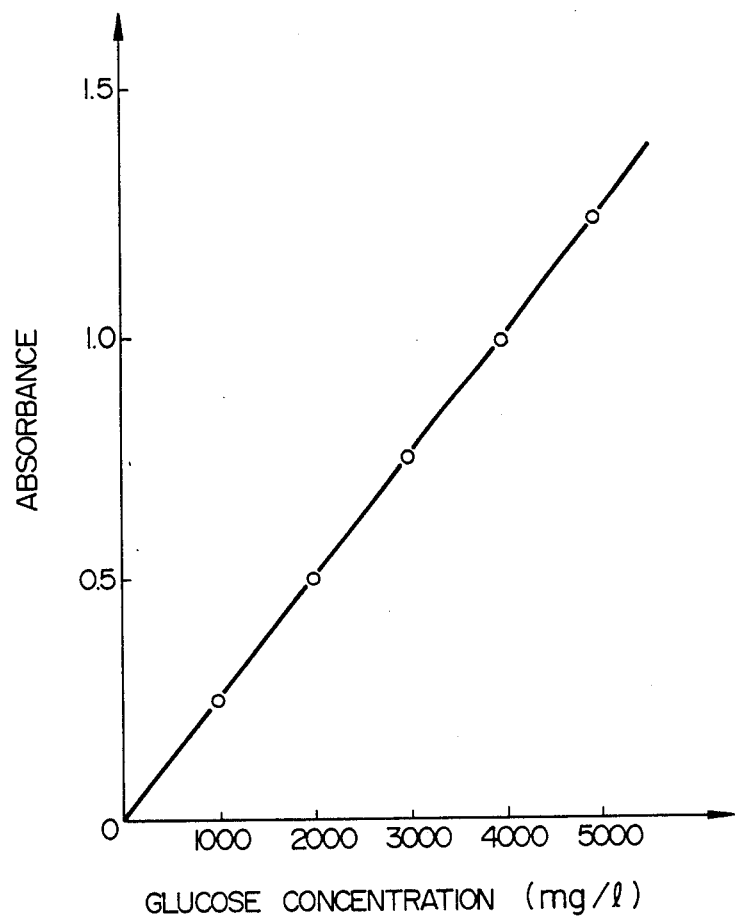
FIG. 5 shows a calibration curve obtained in Example 4.

On the other hand, glucose standard solutions were prepared by making the concentration of glucose in water 1,000, 2,000, 3,000, 4,000 and 5,000 mg/l respectively. A 10-μl standard solution was treated in the same manner as mentioned above to obtain a calibration curve as shown in FIG. 5 from the absorbances obtained. Glucose concentration in serum was obtained from FIG. 5.

Measured results are shown in Table 2.

REFERENCE EXAMPLE 2

(Determination of Glucose in Serum)

A color developing reagent solution was prepared by dissolving 30,000 U/l of glucose oxidase, 10,000 U/l of peroxidase, 100 mg/l of 4-aminoantipyrine, 500 mg/l of N,N-diethylaniline, and 1,000 mg/l of sodium azide in 0.05 M phosphate buffer (pH 7.0).

To each 10 μl of the same serum as used in Example 4, 3.0 ml of the color developing reagent solution was added and incubated at 37° C. for 20 minutes, followed by measurement of absorbance at 550 nm using reagent blank as control (Ex).

A solution in an amount of 10 μl was taken out from a glucose aqueous solution containing glucose in an amount of 1,000 mg/l and absorbance was measured in the same manner as in the case of measuring the serum (Es).

Glucose concentration in serum can be calculated as follows:

$$\text{Glucose (mg/l)} = \frac{Ex}{Es} \times 1,000.$$

Measured results are shown Table 2. As is clear from Table 2, the values obtained in Example 4 are in good agreement with those of Reference Example 2 and no significant difference is admitted.

TABLE 2

| Serum No. | Example 4 [X] | Reference Example 2 [Y] |
|---|---|---|
| 1 | 835 (mg/l) | 861 (mg/l) |
| 2 | 2640 | 2652 |
| 3 | 472 | 458 |
| 4 | 1507 | 1531 |
| 5 | 726 | 715 |
| 6 | 611 | 606 |
| 7 | 1875 | 1821 |
| 8 | 3697 | 3673 |
| 9 | 825 | 823 |
| 10 | 1192 | 1159 |
| Average | 1438.0 | 1429.9 |
| SD | 1036.4 | 1032.2 |

$Y = 0.995X - 0.9$ ($\gamma = 0.9998$)

EXAMPLE 5

(Determination of $H_2O_2$)

A color developing reagent solution was prepared in the same manner as described in Example 1, except for using 0.67 mmol/l of NADPH in place of NADH.

Using the color developing reagent solution, absorbances of the same aqueous $H_2O_2$ solutions as used in Example 1 were measured in the same manner as described in Example 1.

Figure 6:
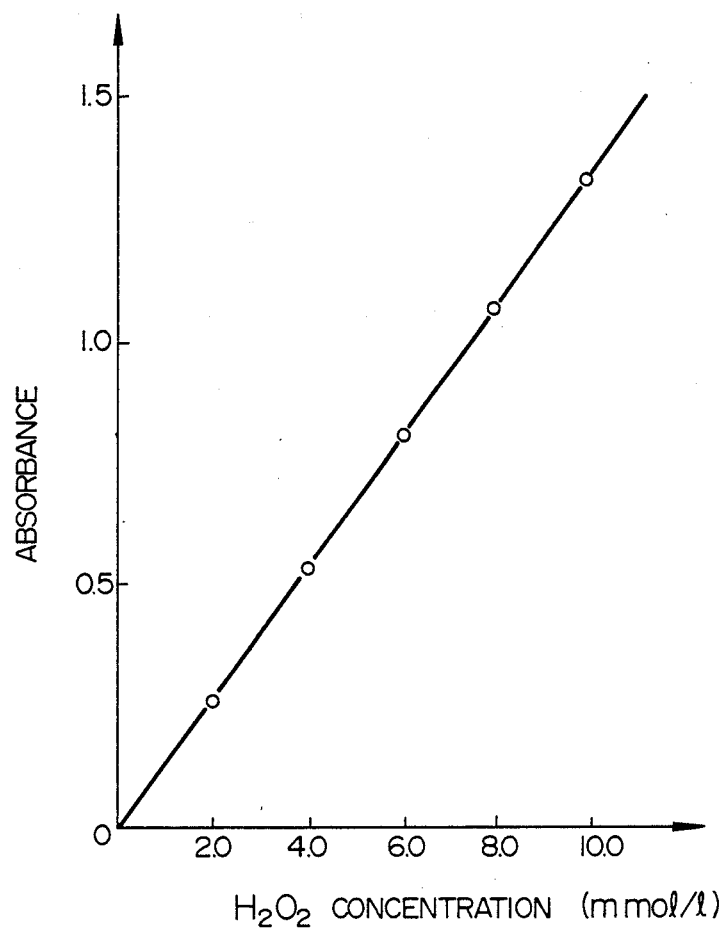
FIG. 6 shows a calibration curve obtained in Example 5.

FIG. 6 shows a relationship between the $H_2O_2$ concentration and the absorbance. As is clear from FIG. 6, a calibration curve obtained by lining plots of 6, a calibration curve obtained by lining plots of absorbances corresponding to individual $H_2O_2$ concentrations (mmol/l ) is a linear line passing through the origin. This means that the calibration curve shows good quantitativeness.

EXAMPLE 6

(Influence of Reducing Substances)

A color developing reagent solution (Reference Example 3) was prepared by dissolving 0.05% w/v of TOOS, 0.01% w/v of 4-aminoantipyrine, 100 U/l of cholesterol oxidase, 3,000 U/l of peroxidase, and 0.15% w/v of Triton X-100 in 0.1 M of phosphate buffer (pH 7.0).

To each 50 μl of samples obtained by adding ascorbic acid or bililubin in amounts as listed in Table 3 or 4 to human pool serum, 3 ml of the color developing reagent solution was added and incubated at 37° C. for 15 minutes, followed by measurement of absorbance at 555 nm using reagent blank as control (Ex). Using a cholesterol standard solution (cholesterol 1,000 mg/l), absorbance (Es) was obtained in the same manner as described in the procedure of serum to calculate the free cholesterol concentration in serum by the following equation:

$$\text{Cholesterol concentration (mg/l)} = \frac{Ex}{Es} \times 1,000$$

Measured results are shown in Table 3 and 4.

On the other hand, the color developing reagent solution used in Example 2 was also subjected to the same procedure as mentioned above to know an influence of ascorbic acid or bilirubin.

The results are also shown in Tables 3 and 4.

As is clear from Tables 3 and 4, the influence of ascorbic acid or bililubin is remarkably low in the color developing reagent solution used in this invention.

TABLE 3

| | Reagent | |
|---|---|---|
| Ascorbic acid | Example 2 | Reference Example 3 |
| 0 (mg/l) | 460 mg/l | 460 (mg/l) |
| 50 | 440 | 290 |
| 100 | 360 | 180 |
| 150 | 330 | 110 |
| 200 | 310 | 60 |
| 300 | 290 | 20 |
| 400 | 260 | 10 |
| 500 | 240 | 10 |

TABLE 4

| | Reagent | |
|---|---|---|
| Bililubin | Example 2 | Reference Example 3 |
| 0 (mg/l) | 460 (mg/l) | 460 (mg/l) |
| 50 | 450 | 410 |
| 100 | 450 | 370 |
| 150 | 430 | 340 |
| 200 | 400 | 320 |

EXAMPLE 7

(Measurement of POD activity)

[Preparation of reagent solutions]

① Color producing reagent solution

A color producing reagent solution was prepared by dissolving 0.02% w/v of nitro-TB, 0.67 mmol/l of NADH, 0.02% w/v of phenol and 0.05% w/v of Triton X-100 in 0.05 M phosphate buffer (pH 6.0).

② $H_2O_2$ solution

An aqueous solution containing 2.94 mmol/l of $H_2O_2$ was prepared.

③ POD standard solutions

Aqueous solutions containing 0.06, 0.12, 0.18, 0.24 and 0.3 mg/dl of POD Type III (120 U/mg) (mfd. by Toyobo Co., Ltd., Japan) were prepared.

④ Reaction stopper solution

A 2% aqueous solution of sodium dodecylsulfate was prepared.

[Measuring method]

To 20 μl of POD standard solution, 3 ml of the color developing reagent solution was added, and 0.1 ml of the $H_2O_2$ solution was added, followed by incubation at 37° C. for 10 minutes. After addition and mixing of 1.0 ml of the reaction stopper solution, absorbance at a wavelength of 560 nm was measured using reagent blank as control.

Figure 7:
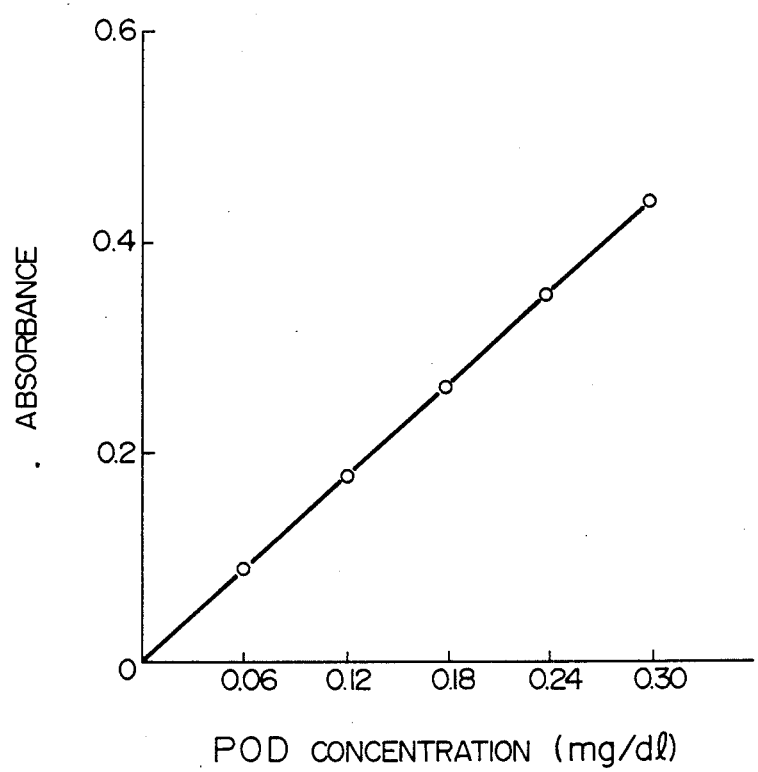
FIG. 7 shows a calibration curve obtained in Example 7.

FIG. 7 shows a relationship between the POD concentration and the absorbance. As is clear from FIG. 7, the calibration curve obtained by lining plots of absorbances corresponding to individual POD concentrations (mg/dl) shows good quantitativeness.

The same results were obtained when 0.03% w/v of TOOS was used in place of 0.02% w/v of phenol in the color producing reagent solution.

EXAMPLE 8

(Substrate Staining)

A substrate staining solution was prepared by dissolving 0.06% w/v of nitro-TB, 1.3 mmol/l of NADPH, 0.005% w/v of phenol, and 0.008% w/v of $H_2O_2$ in 0.05 M phosphate buffer (pH 6.0).

Staining of nerve cells of supraoptic nucleus was carried out by using antivasopressin antibody. Slices of hypothalamus posterior pututiary tissue subjected to PAP treatment were dipped in the substrate staining solution and incubated at room temperature for 30 minutes. Then, the slices were washed with distilled water to prepare stained preparations. The obtained stained preparations showed good staining properties and no fading with the lapse of time.

The same results were obtained when 0.008% w/v of TOOS or 0.008% w/v of α-naphthol was used in place of 0.005% w/v of phenol in the substrate staining solution.

EXAMPLE 9

(Measurement of POD Activity on Nitrocellulose Membrane)

[Preparation of reagent solutions]

① Staining reagent solution

A staining reagent solution was prepared by dissolving 0.03% w/v of nitro-TB, 1.4 mmol/l of NADH and 0.025% w/v of phenol in 0.05 M phosphate buffer (pH 7.0).

② $H_2O_2$ solution

An aqueous solution containing 2.94 mmol/l of $H_2O_2$ was prepared.

③ POD standard solutions

POD standard solutions were prepared by diluting affinity purified goat anti-rabbit. IgG (H+L)-horseradishperoxidase conjugate (mfd. by Bio-Rad Laboratories, Richmond, CA, hereinafter referred to as "IgG-HRP") with 20 mmol/l of tris(hydroxymethyl)aminomethane-HCl buffer (pH 7.5) containing 0.5 mol/l of NaCl (hereinafter referred to as "Tris-HCl buffer") so as to give IgG-HRP concentrations of 0.0625, 0.125, 0.25, 0.50, 0.75 and 1.0 μl/ml.

[Measuring method]

To each well of a Bio-Dot apparatus (mfd. by Bio-Rad Laboratories, Richmond, CA) assembled with a sheet of nitrocellulose membrane equilibrated with the Tris-HCl buffer, 400 μl of each concentration of POD standard solutions was applied and filtered naturally. After washing and blocking with the Tris-HCl buffer, the nitrocellulose membrane was taken out by disassembling the apparatus and dipped in 10 ml of the staining reagent solution added with 20 μl of the $H_2O_2$ aqueous solution to begin the reaction. After reacting at 25° C. for 30 minutes, the nitrocellulose membrane was washed with purified water, dried, treated with decalin and measured with a densitometer (Bio-Rad Model 1650).

Figure 8:
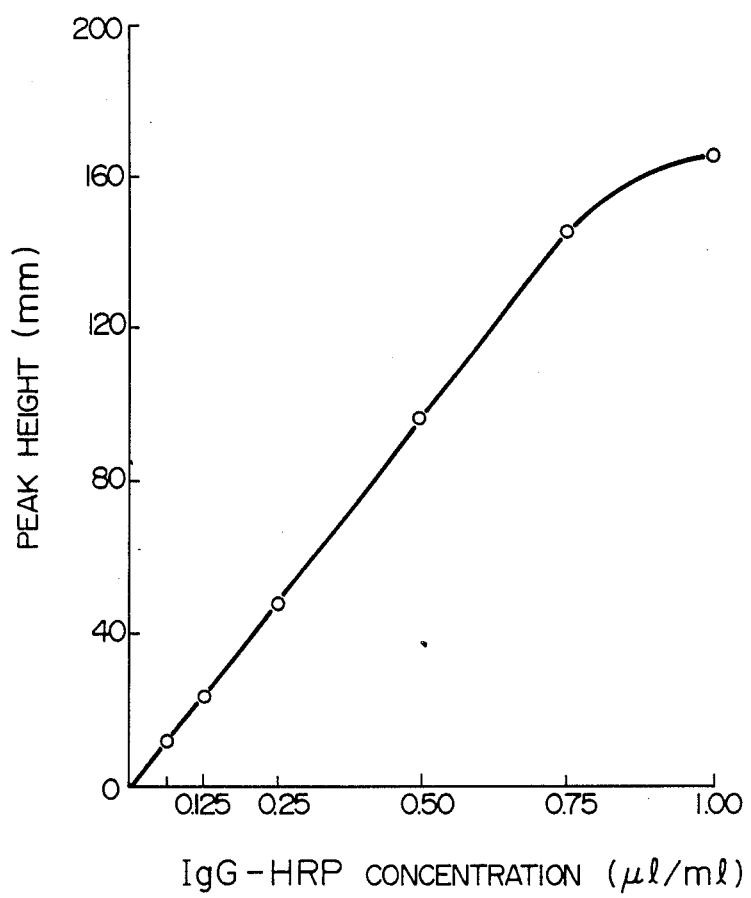
FIG. 8 shows a calibration curve obtained in Example 9.

FIG. 8 shows a relationship between the POD (IgG-HRP) concentration (μl/ml) and the peak height of densitogram obtained. As is clear from FIG. 8, the calibration curve obtained by lining the plots of peak height corresponding to individual POD (IgG-HRP) concentrations shows good quantitativeness.

The same results were obtained when 0.05% w/v of TOOS was used in place of 0.025% w/v of phenol in the staining reagent solution.

EXAMPLE 10

(Determination of α-Fetoprotein (AFP))

[Preparation of reagent solutions]

① Staining reagent solution

A staining reagent solution was prepared by dissolving 0.03% w/v cf nitro-TB, 2.8 mmol/l of NADH, and 0.020% w/v of phenol in 0.05 M phosphate buffer (pH 7.0).

② $H_2O_2$ solution

An aqueous solution containing 2.94 mmol/l of $H_2O_2$ was prepared.

③ AFP standard solutions

AFP standard solutions were prepared by diluting a Japanese AFP standard solution (1000 ng/ml) (manufactured by Nippon Bio-Test Laboratories, Tokyo) with 0.05 M phosphate buffer (pH 7.2) containing 0.15 M of NaCl and 0.3% w/v of bovine albumin so as to give the AFP concentrations of 3.125, 6.25, 12.5, 25, 50, 100, and 200 ng/ml.

④ Preparation of antihuman AFP antibody coated nitrocellulose membrane

In Tris-HCl buffer containing 10 μg/ml of affinity purified antihuman AFP antibody (horse), a nitrocellulose membrane (5×9.2 cm) was dipped for 30 minutes for equilibration. Then, the nitrocellulose membrane from which superfluous moisture had been removed by a filter paper was allowed to stand in a vapor of glutaraldehyde for 30 minutes for coating operation. Then, it was subjected to neutralization treatment with Tris-HCl buffer containing 0.02% w/v of $NaBH_4$, followed by washing with the Tris-HCl buffer. Then, it was dipped in a Tris-HCl buffer containing 0.5% w/v of Tween 20 (polyoxyethylene sorbitan monolaurate, trade name, mfd. by Kao Atlas Co., Ltd.) for 30 minutes to conduct the block treatment, followed by washing with the Tris-HCl buffer to give an antihuman AFP antibody coated nitrocellulose membrane (hereinafter referred to as "antihuman AFP-NC membrane").

[Measuring method]

To each well of a Bio-Dot apparatus assembled with a sheet of the antihuman AFP-NC membrane equilibrated with the Tris-HCl buffer, 40 μl of each concentration of AFP standard solutions was applied and filtered naturally. After washing with the Tris-HCl buffer, the membrane was taken out by disassembling the apparatus and washed with 10 ml of a Tris-HCl buffer containing 0.05% w/v of Tween 20 twice (5 minutes ×2). The resulting membrane was dipped in 10 ml of a rabbit immunoglobulins to human AFP [DACO-immunoglobulins, Copenhagen, Denmark] diluted in 500 times with a Tris-HCl buffer containing 1% w/v of gelatin for 30 minutes, and washed with 10 ml of a Tris-HCl buffer containing 0.05% w/v of Tween 20 twice (10 minutes ×2). Then, the membrane was dipped in an IgG-HRP solution diluted in 1000 times with a Tris-HCl buffer containing 1% w/v of gelatin, and washed with 10 ml of a tris-HCl buffer containing 0.05% w/v of Tween 20 twice (10 minutes ×2).

The thus obtained membrane was subjected to staining treatment in the same manner as described in Example 3, followed by the measurement in the same manner as described in Example 3.

Figure 9:
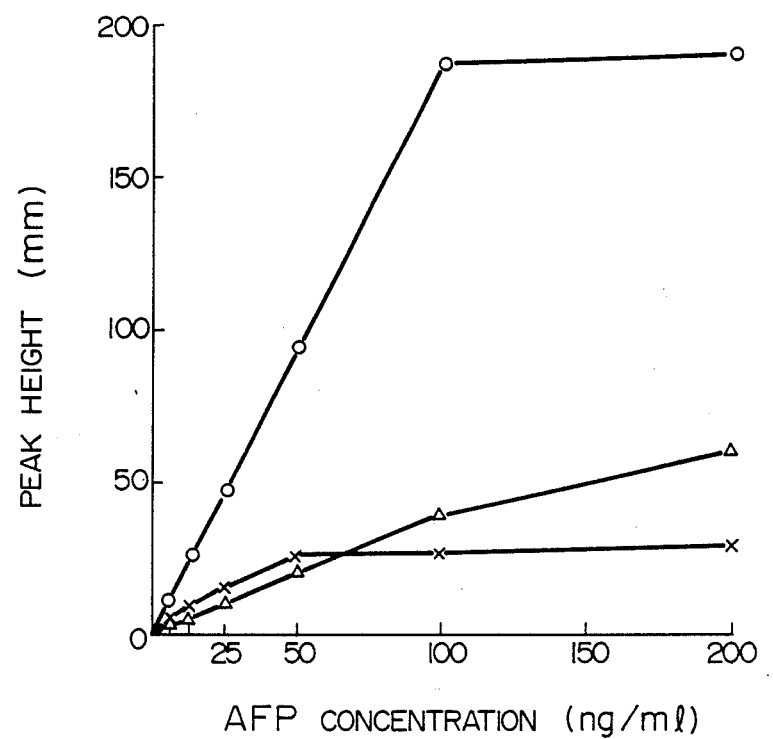
FIG. 9 shows calibration curves obtained in Example 10 and Comparative Examples 1 and 2.

FIG. 9 shows a relationship between the AFP concentrations (ng/ml) and the peak heights of densitogram obtained (shown by -o-o-).

COMPARATIVE EXAMPLE 1

The process of Example 10 was repeated except for using the following staining reagent solution in place of the staining reagent solution and the $H_2O_2$ solution used in Example 10.

(1) Staining reagent solution (containing $H_2O_2$ solution)

A staining reagent solution was prepared by dissolving 0.025% w/v of 3,3'-diaminobenzidine and 0.005% w/v of $H_2O_2$ in 0.05 M tris(hydroxymethyl)amino-methane-HCl buffer (pH 7.6).

The results are shown in FIG. 9 with the curve of -x-x-.

COMPARATIVE EXAMPLE 2

The process of Example 10 was repeated except for using the following staining reagent solution in place of the staining reagent solution and the $H_2O_2$ solution used in Example 10.

(1) Staining reagent solution (containing $H_2O_2$ solution)

A staining reagent solution was prepared by dissolving 0.05% w/v of 4-chloro-1-naphthol and 0.015% w/v of $H_2O_2$ in 0.05 M tris(hydroxymethyl)aminomethane-HCl buffer (pH 7.6) (using methanol as dissolution assistant).

The results are shown in FIG. 9 with the curve of -Δ-Δ-.

As is clear from FIG. 9, the process of Example 10 belonging to this invention is remarkably excellent in the measuring sensitivity and liniarity of the calibration curve compared with those of Comparative Examples 1 and 2 belonging to prior art processes.

As mentioned above, the determination of the amount of $H_2O_2$ or POD activity according to this invention can be remarkably reduced in the influence of reductive materials such as ascorbic acid, bilirubin, etc. present in samples. Further, the staining properties according to this invention are remarkably good and stained portions can be stored for a long period of time without fading. In addition, the sensitivity of the color producing reagents to be reduced used in this invention is several times as high as that of oxidizable color reagents such as 3,3'-diaminobenzidine, 4-chloro-1-naphthol, etc.

What is claimed is:

1. A process for the determination of the amount of hydrogen peroxide or peroxidase activity in a clinical sample, which comprises:
    adding to a clinical sample a reagent composition comprising (a) a reduced form coenzyme selected from the group consisting of NADH and NADPH, (b) a reagent selected from the group consisting of amines, phenols and naphthols, (c) a tetrazolium salt as a color producing reagent to be reduced and (d) peroxidase or an aqueous solution of hydrogen peroxide,
    measuring a change in absorbance and
    calculating the amount of hydrogen peroxide or peroxidase activity from the change in absorbance.

2. A process according to claim 1, wherein the component (d) is peroxidase and the amount of $H_2O_2$ is determined.

3. A process according to claim 1, wherein the component (d) is an aqueous solution of hydrogen peroxide and peroxidase activity is determined.

4. A process according to claim 1 which is conducted in the absence of diaphorase or a thiol compound.

5. A process for determining the amount of hydrogen peroxide in a clinical sample, which comprises:
    adding to a clinical sample a reagent composition comprising (a) a reduced form coenzyme selected from the group consisting of NADH and NADPH, (b) a reagent selected from the group consisting of amines, phenols and naphthols, (c) a tetrazolium salt as a color producing reagent to be reduced, (d) peroxidase,
    incubating the resulting mixture,
    measuring a change in absorbance, and
    calculating the amount of hydrogen peroxide from the change in absorbance.

6. A process according to claim 5, wherein the reagent composition which is added to the clinical sample further comprises an oxidase which is specific to a substrate present in said clinical sample, the concentration of which is to be measured.

7. A process according to claim 5 which is conducted in the absence of diaphorase or a thiol compound.

8. A process for determining peroxidase activity in a clinical sample, which comprises:
    adding to a clinical sample a reagent solution comprising (a) a reduced form coenzyme selected from the group consisting of NADH and NADPH, (b) a reagent selected from the group consisting of amines, phenols and naphthols, and (c) a tetrazolium salt as a color producing reagent to be reduced, and (d) an aqueous solution of hydrogen peroxide,
    incubating the resulting mixture, and if necessary, adding a reaction stopper to the mixture,
    measuring a change in absorbance, and
    calculating the peroxidase activity from the change in absorbance.

9. A process according to claim 8 which is conducted in the absence of diaphorase or a thiol compound.

10. In an immunoperoxidase staining method comprising fixing a substance to be measured on a supporter, labeling peroxidase on the substance to be measured using an antigen-antibody reaction, reacting the peroxidase-labeled substance with a staining reagent, and measuring a color produced, the improvement wherein the staining reagent is a composition comprising (a) a reduced form coenzyme selected from the group consisting of NADH and NADPH, (b) a reagent selected from the group consisting of amines, phenols and naphthols, (c) a tetrazolium salt as a color producing reagent to be reduced, and (d) an aqueous solution of hydrogen peroxide.

11. In an enzyme immunoassay using peroxidase as a labeling enzyme comprising the steps of reacting solid-phase antibody with an antigen to form an insoluble complex, reacting the solid-phase absorbed antigen with excess labeled antibody to form a peroxidase-labeled complex, reacting the peroxidase labeled complex with a staining agent, and measuring a color produced, the improvement wherein the staining reagent is a composition comprising (a) a reduced form coenzyme selected from the group consisting of NADH and NADPH, (b) a reagent selected from the group consisting of amines, phenols and naphthols, (c) a tetrazolium salt as a color producing reagent to be reduced, and (d) an aqueous solution of hydrogen peroxide.

12. In an enzyme immunoassay using peroxidase as a labeling enzyme comprising the steps of reacting (a) peroxidase labeled substance to be measured, (b) an antibody for the substance to be measured, and (c) a sample containing the substance to be measured, followed by reacting a second antibody for said antibody (b) with the above mixture of (a), (b) and (c), separating an antigen-antibody complex obtained from the bonding of the peroxidase labeled substance and the antibody for the substance to be measured, reacting the antigen-antibody complex with a staining reagent, and measuring a color produced, the improvement wherein the staining reagent is a composition comprising (a) a reduced form coenzyme selected from the group consisting of NADH and NADPH, (b) a reagent selected from the group consisting of amines, phenols and naphthols, (c) a tetrazolium salt as a color producing reagent to be reduced, and (d) an aqueous solution of hydrogen peroxide.

* * * * *